United States Patent
Schmitt

(10) Patent No.: US 6,189,731 B1
(45) Date of Patent: Feb. 20, 2001

(54) DEVICE FOR HOLDING AND DISPENSING COTTON SWABS

(76) Inventor: Rolf-Peter Schmitt, Feincheswiese, 56424 Staudt (DE)

(*) Notice: Under 35 U.S.C. 154(b), the term of this patent shall be extended for 0 days.

(21) Appl. No.: 09/301,052

(22) Filed: Apr. 28, 1999

(30) Foreign Application Priority Data

Apr. 29, 1998 (DE) .............................................. 298 07 696

(51) Int. Cl.[7] .................................................. B65E 59/00
(52) U.S. Cl. ........................ 221/103; 221/196; 221/264; 221/276; 221/281
(58) Field of Search .................................. 221/103, 110, 221/111, 195, 196, 264, 271, 281, 95, 276

(56) References Cited

U.S. PATENT DOCUMENTS

| 1,507,999 | * | 9/1924 | Hubbard | 221/281 |
| 1,607,014 | * | 11/1926 | Moak | 221/264 |
| 3,445,037 | * | 5/1969 | Rothbaum | 221/196 |
| 4,896,792 | * | 1/1990 | Marchand | 221/103 |
| 5,667,097 | * | 9/1997 | Joyce | 221/264 |

FOREIGN PATENT DOCUMENTS

| 665123 | * | 9/1929 | (FR) | 221/195 |
| 788093 | * | 12/1957 | (GB) | 221/103 |
| 1215940 | * | 3/1986 | (SU) | 221/103 |

* cited by examiner

*Primary Examiner*—H. Grant Skaggs
(74) *Attorney, Agent, or Firm*—Friedrich Kueffner

(57) ABSTRACT

A device for holding and dispensing cotton swabs or the like, wherein the device includes a housing for holding the cotton swabs and the housing has at least two chambers extending parallel one behind the other for holding with play a plurality of cotton swabs arranged one above the other, wherein the chambers have an inclined bottom. The frontmost chamber is connected to a slide member which holds only a single cotton swab. A dispensing chamber is arranged underneath the slide member, wherein a separating wall between two successive chambers can be raised as required by a predetermined dimension.

6 Claims, 1 Drawing Sheet

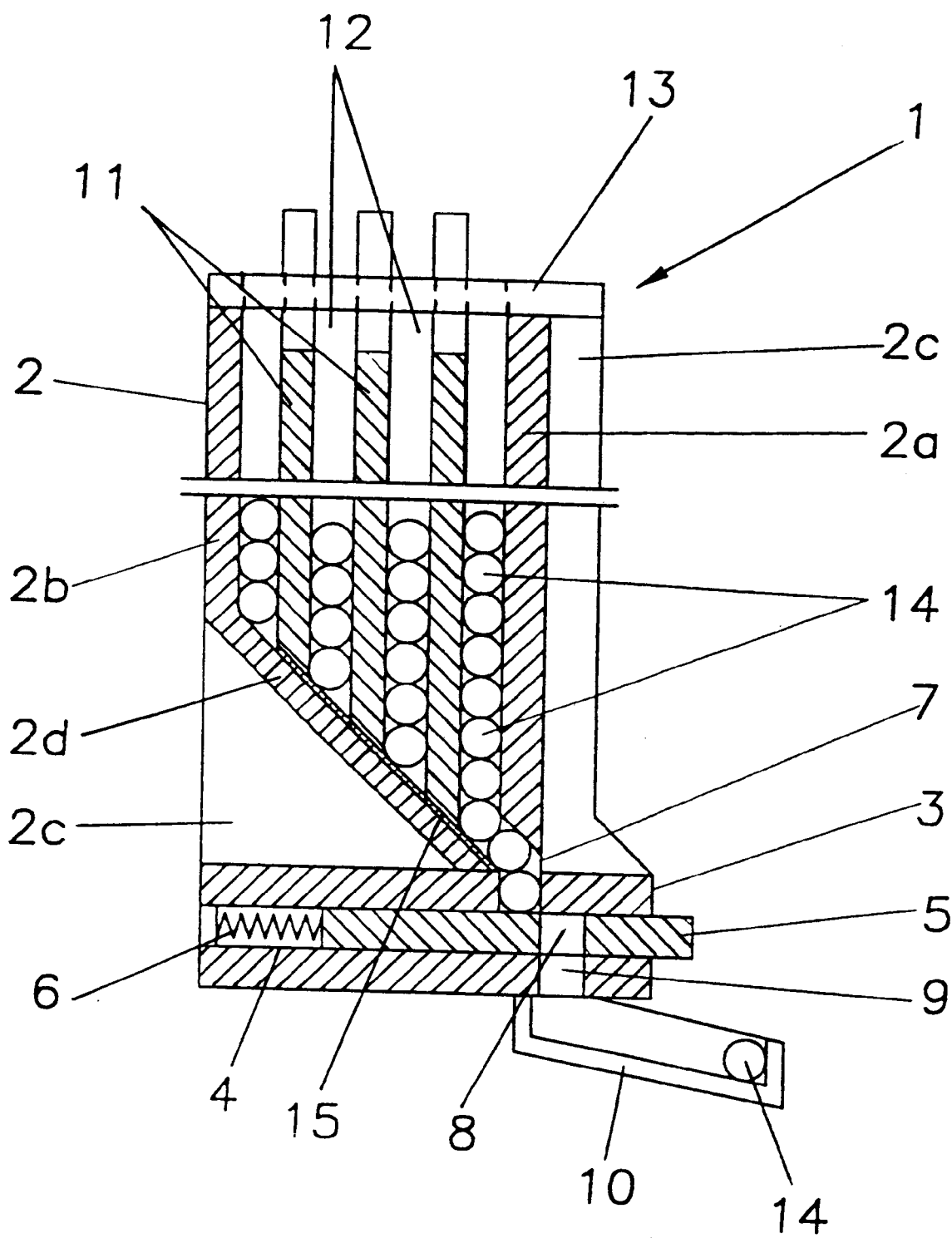

DEVICE FOR HOLDING AND DISPENSING COTTON SWABS

BACKGROUND OF THE INVENTION

1. Field of the Invention

The present invention relates to a device for holding and dispensing cotton swabs or the like, wherein the device is comprised of a housing for holding the cotton swabs.

2. Description of the Related Art

Cotton swabs are offered in special containers or packagings, in many cases in jars with covers. After the containers are purchased, they are usually placed in cabinets in bathrooms and the cotton swabs are taken out of the containers as needed for use. Depending on the type of packaging, it is extremely difficult to remove the cotton swabs by hand from the containers. In many cases, more than one cotton swab are grasped or one cotton swab adheres to another and then again drops back into the container and causes the cotton swabs to be irregularly arranged in the container, so that the removal of the cotton swabs is made more difficult. Moreover, it is frequently considered time consuming when a cotton swab is needed quickly to have to first open a cabinet and a container, wherein the cabinet and the container then have to be closed again.

SUMMARY OF THE INVENTION

Therefore, it is the primary object of the present invention to provide a device for holding and dispensing cotton swabs or the like which ensures that the cotton swabs are securely stored and which ensures that always only one cotton swab can be removed without any problems.

In accordance with the present invention, in a device of the above-described type, the housing has at least two chambers extending parallel one behind the other for holding with play a plurality of cotton swabs arranged one above the other, wherein the chambers have an inclined bottom, wherein the frontmost chamber is connected to a slide member which holds only a single cotton swab, wherein a dispensing chamber is arranged underneath the slide member, and wherein a separating wall between two successive chambers can be raised as required by a predetermined dimension.

In a device constructed in accordance with the present invention, the cotton swabs are initially filled individually into the chambers. By moving the slide member, always only one cotton swab is transferred into the dispensing chamber in which it can then be easily grasped and removed. Searching for cotton swabs as was necessary in the past is not required. The device according to the present invention can be fastened in a simple manner to a wall, for example, in a bathroom.

In accordance with an advantageous feature, the device or its housing can be integrated with other housings which hold toothpaste, toothbrushes, paper napkins or cotton pads, so that a large structural unit is formed which always makes those items which are required in a bathroom easily accessible.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

BRIEF DESCRIPTION OF THE DRAWING

In the drawing:

The single FIGURE of the drawing is a sectional view of the device according to the present invention.

DESCRIPTION OF THE PREFERRED EMBODIMENTS

The drawing is a schematic illustration of a device 1 for holding and dispensing cotton swabs 14. The device 1 includes a housing 2, for example, of transparent synthetic material, and with a rectangular cross-section. The housing 2 has a front wall 2a, a rear wall 2b and two side walls 2c. Extending downwardly, for example, at an angle of 45° from the rear wall 2b is a bottom 2d, wherein the bottom 2d extends approximately to the inner surface of the front wall 2a. In the lower portion of the housing, the side walls 2c as well as the bottom 2d extend into a base plate 3. In the illustrated embodiment, this base plate 3 has a recess 4 in which a slide member 5 is inserted. This slide member 5 is usually biased by at least one pretensioned tension spring 6. In the position of the slide member 5 shown in the drawing, the slide member 5 can only be moved against the force of the spring 6.

Provided in the area between the bottom 2d, the front wall 2a and the base plate 3 is a duct 7 which, in the basic position of the slide member 5 is in communication with a recess 8. In the position of the slide member 5 shown in the drawing, the recess 8 is located above a drop opening 9 which is provided in the base plate 3. A dispensing chamber 10 is located underneath the base plate 3 and, thus, underneath the drop opening 9.

The distance between the two side walls 2c of the housing 2 is slightly greater than the length of the longest cotton swabs 14 which are sold on the market.

Vertical grooves are provided in the inner surfaces of the side walls 2c, wherein separating walls 11 can be inserted from above into the grooves. The separating walls 11 form between themselves and the front wall 2a and the rear wall 2b chambers 12 whose width is slightly greater than the greatest diameter of cotton swabs. For example, by removing a cover 13, the chambers 12 can be filled with cotton swabs 14, as partially illustrated in the drawing.

In the illustrated position of the separating walls 11, the cotton swabs 14 which have been filled into the frontmost chamber 12 drop first into the duct 7 and from there into the recess 8 when the slide member 5 is in its basic position. The lowermost cotton swab 14 then comes to rest on the bottom side of the recess 4 in the slide member 5. Then the slide member 5 in whose recess 8 now is a cotton swab 14 is pulled toward the front by a grip provided on the slide member 5, the cotton swab 14 drops down into the dispensing chamber where it can be removed as already described above.

All separating walls 11 are at the bottom sides thereof provided with a guide plate 15 which extends parallel to the bottom 2c and underneath the cross-section of a chamber 12. When all cotton swabs 14 have been removed from the frontmost chamber 12, the first separating wall 11 together with the guide plate 15 are moved upwardly. This causes the duct 7 to be extended toward the top, so that cotton swabs 14 now drop from the second chamber 12 into the duct 7 and from there through the base plate 3 to the recess 8 of the slide member 5. When this second chamber 12 is also empty, the next separating wall is also pulled upwardly by a predetermined distance, so that now the next chamber 12 is available for dispensing cotton swabs 14. Once all chambers 12 are empty, they are once again filled with cotton swabs.

In accordance with a modified embodiment, it is possible to provide the cover 13 with filling openings through which the cotton swabs 14 can be filled into the chambers 12.

While specific embodiments of the invention have been shown and described in detail to illustrate the inventive principles, it will be understood that the invention may be embodied otherwise without departing from such principles.

I claim:

1. A device for holding and dispensing cotton swabs or the like, the device comprising a housing having a front wall and a rear wall and an inclined bottom, at least one separating wall mounted between the front wall and the rear wall so as to form at least two parallel chambers, arranged sequentially in a rearward direction from the front wall to the rear wall, for holding with play a plurality of cotton swabs placed one above the other, a manually actuated slide member mounted underneath the chambers and having an opening for receiving in a basic position of the slide member a single cotton swab from a frontmost of the at least two chambers, and a dispensing chamber mounted underneath the slide member, wherein the slide member is configured to release the single cotton swab into the dispensing chamber when the slide member is pulled forward from the basic position into a release position, wherein the at least one separating wall is mounted so as to be manually raisable by a predetermined extent as necessary to connect the opening for receiving a single cotton swab to one of the at least two chambers arranged behind the at least one separating wall in the rearward direction.

2. The device according to claim 1, further comprising a pretensioned spring for holding the slide member in the basic position.

3. The device according to claim 1, wherein the at least one separating wall has at a lower end thereof a guide plate having the same inclination as the bottom wall, wherein the guide plate extends toward the front wall to the next separating wall or to the front wall.

4. The device according to claim 1, further comprising a cover with filling openings provided on the housing.

5. The device according to claim 1, wherein the housing has a removable cover.

6. The device according to claim 1, further comprising a base plate connected below the inclined bottom of the housing, wherein the base plate is configured to receive the slide member, wherein the base plate has a duct connecting the opening for receiving a single cotton swab to the frontmost of the at least two chambers.

* * * * *